(12) United States Patent
Trussardi et al.

(10) Patent No.: US 10,337,039 B2
(45) Date of Patent: Jul. 2, 2019

(54) PROCESS FOR THE PREPARATION OF CHIRAL 2-ARYL MORPHOLINES

(71) Applicant: Hoffmann-La Roche Inc., Little Falls, NJ (US)

(72) Inventors: Rene Trussardi, Birsfelden (CH); Hans Iding, Rheinfelden (CH)

(73) Assignee: Hoffmann-La Roche Inc., Little Falls, NJ (US)

( * ) Notice: Subject to any disclaimer, the term of this patent is extended or adjusted under 35 U.S.C. 154(b) by 209 days.

(21) Appl. No.: 15/175,779

(22) Filed: Jun. 7, 2016

(65) Prior Publication Data

US 2016/0289718 A1    Oct. 6, 2016

Related U.S. Application Data

(63) Continuation of application No. PCT/EP2014/076831, filed on Dec. 8, 2014.

(30) Foreign Application Priority Data

Dec. 11, 2013 (EP) .................... 13196638

(51) Int. Cl.
| | |
|---|---|
| C12P 7/02 | (2006.01) |
| C12P 7/22 | (2006.01) |
| C12P 13/00 | (2006.01) |
| C12P 17/14 | (2006.01) |
| C07D 265/30 | (2006.01) |

(52) U.S. Cl.
CPC ............ C12P 17/14 (2013.01); C07D 265/30 (2013.01); C12P 7/02 (2013.01); C12P 7/22 (2013.01); C12P 13/008 (2013.01); Y02P 20/55 (2015.11)

(58) Field of Classification Search
None
See application file for complete search history.

(56) References Cited

U.S. PATENT DOCUMENTS

2012/0245172 A1   9/2012   Galley et al.

FOREIGN PATENT DOCUMENTS

| EA | 200500801 A1 | 12/2005 |
|---|---|---|
| WO | 02/086126 | 10/2002 |
| WO | 2004/052372 A1 | 6/2004 |
| WO | 2006/045598 | 5/2006 |

OTHER PUBLICATIONS

ISR for PCT/EP2014/076831
Kapoor et al., "Synthesis of β-adrenergic blockers (R)-(−)-nifenalol and (S)-(+)-sotalol via a highly efficient resolution of a bromohydrin precursor" Tetrahedron: Asymmetry 16:717-725 (2005).
Sawant et al., "Intamolecular reductive animation stragegy to the synthesis of (R)-N-Boc-2-hydroxymethylmorpholine, N-(3,4-dichlorobenzyl)(R)-2-hydroxymethylmorpholine, and (R)-2-benzylmorpholine" Tetrahedron 66:2010-2014 (2010).
Zindell et al., "Morpholine containing CB2 selective agonists" Bioorganic & Medicinal Chemistry Letters 19:1604-1609 (2009).
Fabricio R. Bisogno et al., "Chemo- and Stereodivergent Preparation of Terminal Epoxides and Bromohydrins through One-Pot Biocatalysed Reactions: Access to Enantiopure Five- and Six-Membered N-Heterocycles" Advanced Synthesis & Catalysis 352:1657-1661 ( 2010).

*Primary Examiner* — Paul J Holland
(74) *Attorney, Agent, or Firm* — Brian L. Buckwalter

(57) ABSTRACT

The invention relates to a novel process for the preparation of chiral 2-(4-aminophenyl) morpholines of the formula

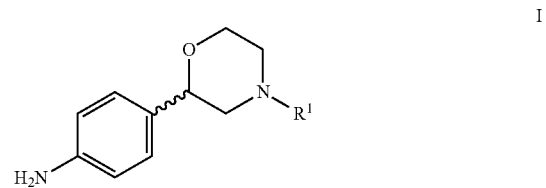

I wherein $R^1$ is hydrogen an amino protecting group.

The chiral 2-(4-aminophenyl) morpholines of the formula I are key intermediates for the preparation of compounds that have a good affinity to the trace amine associated receptors (TAARs).

19 Claims, No Drawings

US 10,337,039 B2

PROCESS FOR THE PREPARATION OF CHIRAL 2-ARYL MORPHOLINES

CROSS REFERENCE TO RELATED APPLICATIONS

This application is a continuation of International Application No. PCT/EP2014/076831 having an international filing date of Dec. 8, 2014 and which claims benefit under 35 U.S.C. § 119 to European Patent Application No. 13196638.4 filed Dec. 11, 2013. The entire contents of both are incorporated herein by reference.

FIELD OF THE INVENTION

The invention relates to novel chemical processes for the manufacture of medicaments and to intermediates useful in their manufacture.

BACKGROUND OF THE INVENTION

The invention relates to a novel process for the preparation of chiral 2-(4-aminophenyl) morpholines of the formula

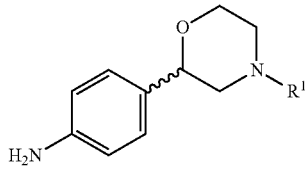

I wherein $R^1$ is hydrogen an amino protecting group.

The chiral 2-(4-aminophenyl) morpholines of the formula I are key intermediates for the preparation of compounds that have a good affinity to the trace amine associated receptors (TAARs), especially for TAAR1 as for instance outlined in PCT Publications WO 2012/016879 and WO 2012/126922.

The invention therefore further relates to the use of the process of the present invention in a process for the preparation (i) of compounds of the formula

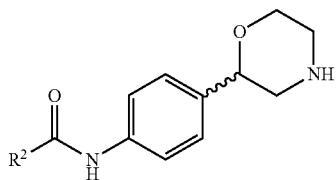

XX wherein:
$R^2$ is aryl or heteroaryl, wherein the aromatic rings are optionally substituted by one or two substituents, selected from $C_{1-7}$-alkyl, halogen, $CF_3$, $OCF_3$, $OCH_2CF_3$, $C_{1-7}$-alkoxy or cyano;
or a pharmaceutically suitable acid addition salts thereof; or,
and (ii) for the preparation of compounds of the formula

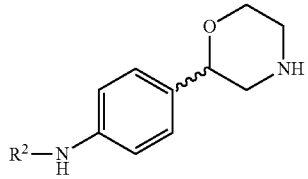

XXX wherein:
$R^2$ is aryl or heteroaryl, wherein the aromatic rings are optionally substituted by one or two substituents, selected from $C_{1-7}$-alkyl, halogen, $CF_3$, $OCF_3$, $OCH_2CF_3$, $C_{1-7}$-alkoxy or cyano;
or pharmaceutically suitable acid addition salts thereof.

The object of the present invention was to find a process which is able to be performed on technical scale.

DETAILED DESCRIPTION OF THE INVENTION

The following definitions are set forth to illustrate and define the meaning and scope of the various terms used to describe the invention herein.

The term "$C_{1-7}$-alkyl" relates to a branched or straight-chain monovalent saturated aliphatic hydrocarbon radical of one to six carbon atoms, preferably one to four, more preferably one to two carbon atoms. This term is further exemplified by radicals as methyl, ethyl, n-propyl, i-propyl, n-butyl, s-butyl or t-butyl, pentyl and its isomers, hexyl and its isomers and heptyl and its isomers.

The term "$C_{1-7}$-alkoxy" refers to a $C_{1-7}$-alkyl group as defined above to which an oxygen atom is attached.

The term "halogen" refers to fluorine, chlorine, bromine or iodine, but particularly to chlorine and bromine.

The term "aryl", relates to an aromatic carbon ring such as to the phenyl or naphthyl ring, preferably the phenyl ring. The term optionally substituted phenyl refers a phenyl group which may be substituted with a $C_{1-4}$ alkyl group, a nitro group or with a halogen atom.

The term "heteroaryl" refers to an aromatic 5 to 6 membered monocyclic ring or 9 to 10 membered bicyclic ring which can comprise 1, 2 or 3 heteroatoms selected from nitrogen, oxygen and/or sulphur, such as pyridinyl, pyrazolyl, pyrimidinyl, benzoimidazolyl, quinolinyl and isoquinolinyl.

The term "pharmaceutically acceptable acid addition salts" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methane-sulfonic acid, p-toluenesulfonic acid and the like.

The term "amino protecting group" refers to an acid or Lewis acid sensitive substituent conventionally used to hinder the reactivity of the amino group. Suitable acid or Lewis acid sensitive amino protecting groups are described in Green T., "Protective Groups in Organic Synthesis", 4$^{th}$ Ed. by Wiley Interscience, 2007, Chapter 7, 696 ff. Suitable amino protecting groups for PG can therefore be selected from Boc (t-butoxycarbonyl), benzyl, 4-methoxybenzyl, benzhydryl, Fmoc (fluorenylmethoxycarbonyl), Cbz (benzyloxycarbonyl), Moz (p-methoxybenzyl carbonyl), Troc (2,2,2-trichloroethoxycarbonyl), Teoc (2-(Trimethylsilyl) ethoxycarbonyl), Adoc (adamantoxycarbonyl), formyl, acetyl or cyclobutoxycarbonyl. More particularly it refers to Boc.

In one embodiment of the present invention there is provided a process for the preparation of a chiral 2-(4-aminophenyl) morpholine of the formula (I) wherein $R^1$ is hydrogen or stands

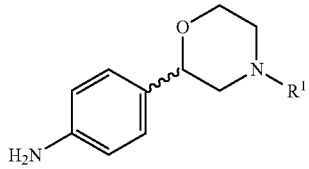

I for an amino protecting group PG comprises the steps:

(a) reducing a ketone of the formula II wherein X is a halogen atom with an

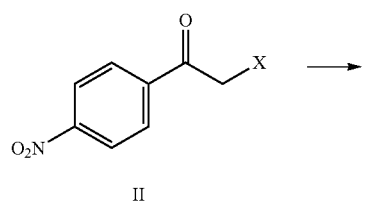

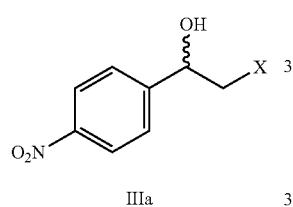

oxidoreductase enzyme to afford the chiral alcohol of the formula IIIa;

(b) displacing the halogen intramolecularly followed by in situ ring opening

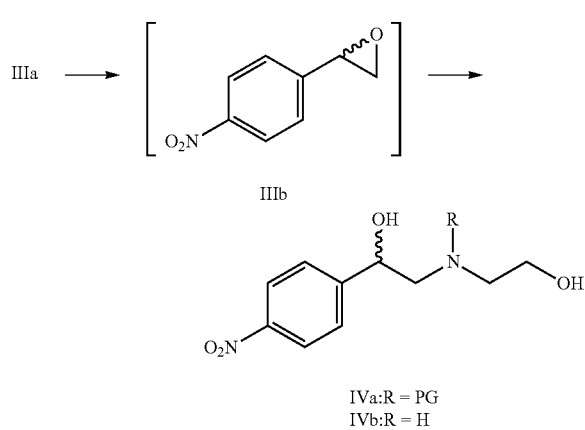

of the resulting epoxide IIIb with ethanolamine to afford IVb;

(c) introducing a protecting group to afford IVa wherein PG is an amino protecting group;

(d) contacting IVa with $R^3SO_2X$ wherein X is a halogen to afford VI;

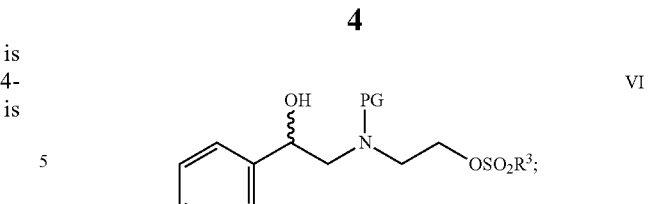

$R^3 = C_{1-4}$ alkyl or optionally substituted phenyl (e) cyclizing VI to afford the chiral morpholine V wherein PG is as defined

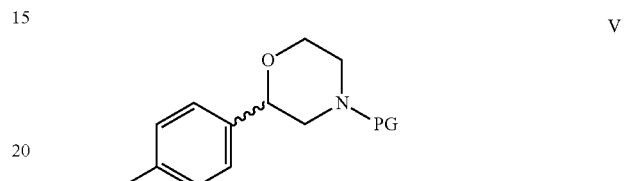

above;

(f) reducing the nitro group to afford chiral 2-(4-aminophenyl) morpholine of the formula I wherein $R^1$ is an amino PG; and, (g) optionally removing the amino protecting group PG to afford a compound of formula I wherein $R^1$ is a H.

In another embodiment of the present invention compound I wherein $R^1$ optionally is an amino protecting group is converted to a compound of formula XX or XXX wherein $R^2$ is aryl or heteroaryl, wherein the aromatic rings are optionally substituted by one or two substituents, selected from $C_{1-7}$-alkyl, halogen, $CF_3$, $OCF_3$, $OCH_2CF_3$, $C_{1-7}$-alkoxy or cyano; or a pharmaceutically suitable acid addition salts thereof.

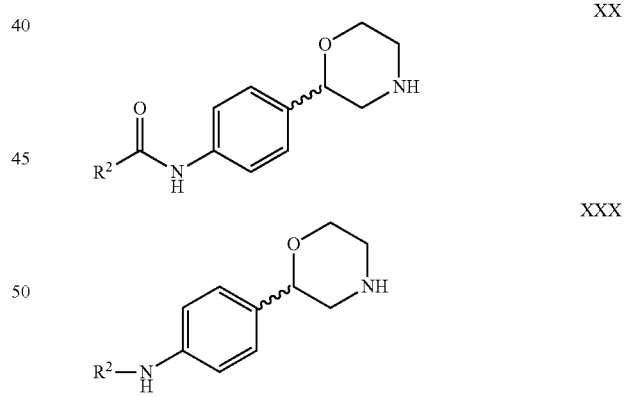

Step a) requires the enzymatic reduction of a ketone of the formula II.

Ketones of the formula II are commercially available or can be synthesized according to methods known to the skilled in the art.

The 2-bromo-1-(4-nitro-phenyl) ethanone is the ketone of formula II particularly used.

The asymmetric reduction is catalyzed by an oxidoreductase, usually in the presence of NADH or NADPH as cofactor, which is regenerated in-situ.

The oxidized cofactor is as a rule continuously regenerated with a secondary alcohol as cosubstrate. Typical cosubstrates can be selected from 2-propanol, 2-butanol, pentan-1,4-diol, 2-pentanol, 4-methyl-2-pentanol, 2-heptanol, hexan-1,5-diol, 2-heptanol or 2-octanol, preferably 2-propanol. Preferably, the cofactor is regenerated by means of the cosubstrate at the same enzyme also catalyzing the target reaction. The acetone formed when 2-propanol is used as cosubstrate is in a further preferred embodiment continuously removed from the reaction mixture.

Also well-known is the cofactor regeneration via an additional enzyme oxidizing its natural substrate and providing the reduced cofactor. For example secondary alcohol dehydrogenase/alcohol; glucose dehydrogenase/glucose; formate dehydrogenase/formic acid; glucose-6-phosphate dehydrogenase/glucose-6-phosphate; phosphite dehydrogenase/phosphite; hydrogenase/molecular hydrogen and the like. In addition electrochemical regeneration methods are known as well as chemical cofactor regeneration methods comprising a metal catalyst and a reducing agent are suitable.

Preferred microbial oxidoreductase enzymes origin from yeasts, bacteria or from mammalian cells.

The oxidoreductase can be applied in the form of the isolated enzyme(s) or the whole cells, optionally in immobilized form by one of the numerous conventional methods described in literature.

In a particular embodiment of the present invention, the asymmetric reduction is performed in an aqueous medium in the presence of an organic cosolvent which can be selected for example from glycerol, 2-propanol, diethylether, tert.butylmethylether, diisopropylether, dibutylether, ethylacetate, butylacetate, heptane, hexane or cyclohexene or from mixtures thereof.

The presence of an organic cosolvent is particularly advantageous as a homogenous suspension can be formed which allows simple separation of the desired ketone of formula II by filtration.

The reaction temperature is usually kept in a range between 1° C. and 50° C., preferably between 20° C. and 40° C.

The reaction concentration (concentration of ketone of formula II and chiral alcohol of formula IIIa in the reaction mixture) is usually kept in a range between 1% and 25%, preferably between 10% and 20%.

Upon termination of the reaction (as a rule >90% conversion) the product is conventionally worked up by extraction or preferred by filtration.

Depending on the ketone substrate the preferred catalyst/cofactor/cosubstrate systems vary.

As a rule oxidoreductases are selected which have the potential to convert the ketone of formula II with an enantiomeric excess of the desired chiral alcohol of the formula IIIa of 98% and above.

For the formation of the (S)-2-bromo-1-(4-nitro-phenyl)-ethanol the following oxidoreductases have been proved to be useful.

NADPH-dependent oxidoreductases can be selected from types KRED-Y1, KRED-NADPH-P1A04, KRED-NADPH-P2H07, KRED-NADPH-P1B10, KRED-NADPH-107, KRED-NADPH-135, KRED-NADPH-136, KRED-NADPH-147 or KRED-NADPH-162 C, which are all available from Codexis Inc., Redwood City, Calif., USA.

Particularly useful is the NADPH-dependent oxidoreductase KRED-Y1, an engineered ketoreductase from *Lactobacillus kefir* as disclosed in PCT Int. Publication No. WO2008103248A1 and identified as SEQ. ID. NO. 124 having an additional E145A substitution, from Codexis Inc., Redwood City, Calif., USA.

NADH dependent oxidoreductases can be selected from types KRED-NADH-110 and KRED-NADH-124 all from Codexis Inc., Redwood City, Calif., USA, from types A161, A291 and A401 from Almac Group Ltd. Craigavon, United Kingdom from type A11 from Johnson Matthey, London, United Kingdom and from 1.1.200 from evocatal GmbH, Monheim am Rhein, Germany from ES-KRED-120 and from Enzysource, Hangzhou, China. Particularly useful is the NADH dependent oxidoreductase KRED-NADH-110 from Codexis Inc., Redwood City, Calif., USA and A11 from Johnson Matthey, London, United Kingdom.

The asymmetric reduction can be performed applying either the enzyme-coupled cofactor regeneration based on glucose as final reductant or the substrate coupled regeneration using 2-propanol as final reductant. During the reductions with glucose as final reductant the pH has to be maintained by controlled addition of a base to neutralize the formed gluconic acid—the oxidized by-product of the reduced nicotinamide cofactor regeneration using glucose dehydrogenase (GDH 105 [Codexis]) in a range of 1/10 to 1/2000 (enzyme/substrate ratio). The reaction temperature can be maintained between 20° C. and 40° C. The reaction can be performed as a conversion of the ketone of formula II to the chiral alcohol of formula IIIa in suspension at concentrations up to 25%. The work up of the product can be achieved by conventional extractive procedures, for instance with TBME or ethyl acetate. The product is preferably isolated by filtration—if advantageous—after prior evaporation of the organic co-solvent.

For the formation of the (R)-2-bromo-1-(4-nitro-phenyl)-ethanol the following oxidoreductases have been proved to be useful.

NADPH-dependent oxidoreductase can be selected from types KRED-NADPH-104, KRED-NADPH-130 or KRED-NADPH-148 all from Codexis Inc., Redwood City, Calif., USA. Particularly useful is the NADPH-dependent oxidoreductase KRED-NADPH-104 from Codexis Inc., Redwood City, Calif., USA.

NADH-dependent oxidoreductase can be selected from the types KRED-Y2, KRED-NADH-117, KRED-NADH-126, all from Codexis Inc., Redwood City, Calif., USA, from the type X1 from Johnson Matthey, London, United Kingdom and from type 127 from Enzysource, Hangzhou, China and from the type A131 from Almac Group Ltd. Craigavon, United Kingdom.

Particularly useful is the NADH-dependent oxidoreductase KRED-Y2, an engineered ketoreductase from *Novosphingobium aromaticivorans* as disclosed in PCT Int. Publication No. WO2011/005527A2 and identified as SEQ. ID. NO. 2, from Codexis Inc., Redwood City, Calif., USA.

The asymmetric reduction was performed by applying the enzyme-coupled cofactor regeneration based on glucose as final reductant. During the reaction the pH was maintained by controlled addition of a base such as aqueous sodium hydroxide to neutralize the formed gluconic acid—the oxidized by-product of the reduced nicotinamide cofactor regeneration using glucose dehydrogenase (GDH 105 from Codexis). The reaction temperature can be maintained between 20° C. and 40° C. The reaction can be performed as a conversion of the ketone of formula II to the chiral alcohol of formula IIIa in suspension at concentrations up to 20%. The work up of the product can be achieved by conventional extractive procedures, for instance with TBME or ethyl acetate. The preferred product isolation is by simple product filtration—if advantageous—after evaporation of organic co-solvents.

Step b)

Step b) requires the formation of the N-protected ethanolamine compound of the formula IVa.

In a particular embodiment the chiral alcohol of formula IIIa obtained from step a) can directly, without its isolation from the reaction mixture, be used in this step b).

In general the formation of the N-protected ethanolamine compound of formula IVa is performed either i) in three steps by, in a first step, converting the chiral alcohol of formula IIIa in the presence of a base into an epoxide of the formula

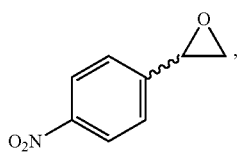

IIIb in a further step converting the epoxide of formula IIIb with ethanolamine into the unprotected ethanolamine compound of formula

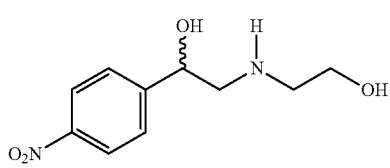

IVb and in a final step by introducing the amino protecting group PG;

ii) in two steps by, in a first step, converting the chiral alcohol of formula IIIa with ethanolamine into the unprotected ethanolamine compound of formula IVb and in a subsequent step by introducing the amino protecting group PG or iii) in one step by converting the chiral alcohol of formula IIIa with an N-protected ethanolamine of the formula

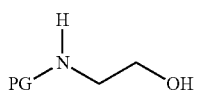

wherein PG stands for an amino protecting group.

Epoxide formation in procedure i) can be accomplished by treatment of the chiral alcohol of formula IIIa with an aqueous base such as with aqueous sodium hydroxide in the presence of an organic solvent such as tetrahydrofuran, methyl tetrahydrofuran, tert.butyl methyl ether, cyclopentyl methyl ether, 1,2-diethoxyethan or with lower aliphatic alcohols such as with ethanol. The epoxide of formula IIIb can be isolated from the organic layer by evaporation of the solvent.

The formation of the unprotected ethanolamine compound of formula IVa in procedure i) can be performed by treatment of the epoxide of formula IIIb with ethanolamine in the presence of an organic base such as triethylamine, N,N-diisopropylethylamine or N-methylmorpholine in a suitable organic solvent such as in ether, tetrahydrofuran, dioxane or tert.butyl methyl ether at a temperature of 0° C. to 60° C.

As a rule a stoichiometric excess of 2 to 30 equivalents, preferably an excess of about 10 equivalents of ethanolamine is used.

Isolation of the unprotected ethanolamine compound of formula IVa from the reaction mixture can happen by way of extraction with a suitable solvent such as with a mixture of ethylacetate and water and subsequent concentration of the organic phase.

The introduction of the amino protecting group PG in procedure i) can be performed applying methods well known to the skilled in the art. In a particular embodiment the Boc group is selected and its introduction is accomplished with Boc-anhydride in the presence of a suitable organic solvent such as ether, tetrahydrofuran, dioxane or tert.butyl methyl ether at a temperature of 0° C. to 40° C. The N-protected ethanolamine compound of the formula IVa can be isolated from the organic layer by evaporation of the solvent.

According to procedure ii) the chiral alcohol of formula IIIa is treated with ethanolamine in the presence of a suitable organic solvent such as ether, tetrahydrofuran, dioxane or tert.butyl methyl ether at a temperature of 0° C. to 60° C.

As a rule a stoichiometric excess of 2 to 30 equivalents, preferably an excess of about 10 equivalents of ethanolamine is used.

Isolation of the unprotected ethanolamine compound of formula IVa from the reaction mixture can happen by way of extraction with a suitable solvent such as with a mixture of ethyl acetate and water and subsequent concentration of the organic phase.

The introduction of the amino protecting group PG can be accomplished as described above for procedure i).

According to procedure iii) the N-protected ethanolamine compound of the formula IVa can also be obtained by treatment of the chiral alcohol of formula III with an N-protected ethanolamine preferably with the benzyl-protected ethanolamine in the presence of a suitable solvent such as with n-propanol and with an organic base such as triethylamine, N,N-diisopropylethylamine or N-methylmorpholine at a temperature of 40° C. to reflux temperature of the solvent.

Alternatively procedure iii) can also be accomplished starting from the epoxide of formula IIIb applying reaction conditions as outlined above for procedure iii).

Step c)

Step c) requires the cyclization of the N-protected ethanolamine compound of formula IVa to form the 2-(4-nitrophenyl) morpholine of formula V.

The reaction is as a rule performed stepwise by reacting the N-protected ethanolamine compound of formula IVa with a sulfonylhalogenide of the formula

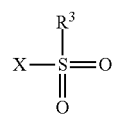

wherein $R^3$ and X are as defined above to form an intermediary sulfonate of the formula

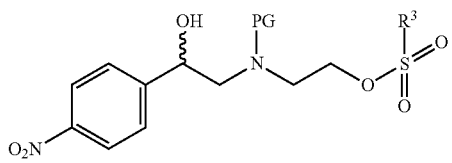

VI wherein PG is as defined above and $R^3$ is $C_{1-4}$ alkyl or phenyl optionally substituted with a $C_{1-4}$ alkyl group, a nitro group or with a halogen atom. A suitable sulfonylhalogenide is the methanesulfonyl chloride ($R^1$=methyl, X=chloro). The reaction is performed in the presence of an organic base such as with triethylamine, N,N-diisopropylethylamine or N-methylmorpholine, particularly triethylamine and a suitable organic solvent such as ether, tetrahydrofuran, dioxane or tert.butyl methyl ether, more particularly tetrahydrofuran at a temperature of 0° C. to 40° C.

The intermediary sulfonate can be isolated using methods known to the skilled in the art, but as a rule the reaction mixture is directly cyclized by treatment with a non nucleophilic base.

Suitable bases are non nucleophilic bases such as alkali metal alkoxides such as potassium tert.butoxide or potassium 2-methyl-2-butoxide, thereby working in a substantially water free environment using suitable non protic organic solvents like ether, tetrahydrofuran, dioxane or tert.butyl methyl ether.

Alternative non nucleophilic bases are phase transfer catalysts such as quaternary ammonium or phosphonium salts tetra alkyl ammonium salts like for instance tetrabutylammonium hydrogen sulfate, benzyltrimethylammonium chloride, ethylhexadecyldimethylammonium bromide or tetrabutylphosphonium bromide. An aqueous inorganic base like aqueous sodium-, potassium- or lithium hydroxide is as a rule present when using this type of bases and a suitable non-protic polar organic solvent such as ether, tetrahydrofuran, 2-methyl tetrahydrofuran or toluene is present as well.

The reaction temperature for the cyclization is selected between 0° C. and 40° C.

The 2-(4-nitrophenyl) morpholine of formula V formed can be isolated by way of extraction with water and a suitable organic solvent, such as with tert.butyl methyl ether and subsequent concentration of the organic phase.

Step d)

Step d) requires the reduction of the nitro group to form the chiral 2-(4-aminophenyl) morpholine of the formula I wherein $R^1$ is PG.

The reduction can be effected by hydrogenation with hydrogen under normal or elevated pressure with a metal hydrogenation catalyst such as a with a $PtO_2$, Pd/C, Pt/V or a Raney Ni catalyst in protic solvents such as in methanol, ethanol, 2-propanol, water or mixtures thereof at temperatures of 0° C. to 40° C.

Isolation of the chiral 2-(4-aminophenyl) morpholine of the formula I wherein $R^1$ is PG can take place by filtration of the reaction mixture and by concentrating the filtrate.

Step e)

Step e) comprises the optional removal of the protecting group PG.

Methods for the removal of amino protecting groups are well known to the skilled in the art.

Removal of the BOC N-protecting group can be effected with aqueous mineral acids such as hydrochloric acid, $H_2SO_4$ or $H_3PO_4$ or organic acids such as trifluoro acetic acid, chloro acetic acid, dichloro acetic acid, acetic acid, methane sulfonic acid or p-toluenesulfonic acid in solvents such as methylene chloride, chloroform, tetrahydrofuran, methanol, ethanol, 1-propanol, acetonitrile or water at a reaction temperature of 0° C. to 80° C.

In a preferred embodiment the removal of the BOC N-protecting group can be effected with trifluoro acetic acid in aqueous acetonitrile at about 60° C. for 2 hours or with aqueous hydro chloric acid 25% in 1-propanol at about 60° C. for 2 hours.

The benzyl protecting group can preferably be removed under hydrogenolysis conditions with a metal hydrogenation catalyst such as with Pd/C.

In a further embodiment of the invention and as outlined above the process of the present invention can be applied in a process for the preparation of compounds of the formula

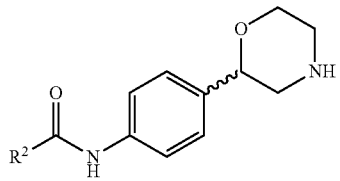

XX wherein
$R^2$ is aryl or heteroaryl, wherein the aromatic rings are optionally substituted by one or two substituents, selected from $C_{1-7}$-alkyl, halogen, $CF_3$, $OCF_3$, $OCH_2CF_3$, $C_{1-7}$-alkoxy or cyano;
or of a pharmaceutically suitable acid addition salt thereof or
for the preparation of compounds of the formula

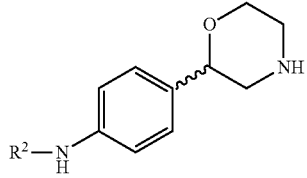

XXX wherein
$R^2$ is aryl or heteroaryl, wherein the aromatic rings are optionally substituted by one or two substituents, selected from $C_{1-7}$-alkyl, halogen, $CF_3$, $OCF_3$, $OCH_2CF_3$, $C_{1-7}$-alkoxy or cyano;
or of a pharmaceutically suitable acid addition salt thereof.

Compounds of the formula XX can for instance be prepared by converting the chiral 2-(4-aminophenyl) morpholine of formula

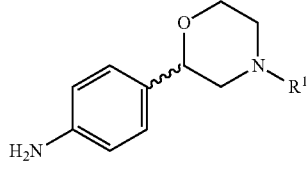

I wherein R¹ is an amino protecting group with the ester of the formula

R²COOR⁴ wherein R² is as above and R⁴ is $C_{1-7}$-alkyl.

In a particular embodiment of the present invention the amide formation can be accomplished by coupling the chiral 2-(4-aminophenyl) morpholine of formula I with the carboxylic acid of the formula

R²COOH wherein R² is as above, with propylphosphonic anhydride as coupling agent. Triethylamine was found to be a suitable base and ethylacetate was found to be a suitable solvent. The reaction temperature can be selected between 0° C. to 50° C.

In a more particular embodiment of the present invention the amide formation can be accomplished by coupling the ester of the formula as outlined above with the chiral 2-(4-aminophenyl) morpholine of formula I in the presence of a suitable alkali alcoholate such as with sodium- or potassium tert. butylate and a suitable organic solvent such as ethereal solvents like tetrahydrofuran, 2-methyl-tetrahydrofuran tert. butyl methyl ether or cyclopentyl methyl ether. The reaction temperature is usually selected between −10° C. to 30° C.

In a subsequent step the amino protecting group can be removed applying methods described under step e) above.

In a further embodiment of the present invention compounds of the formula XX can also be prepared by converting the chiral 2-(4-aminophenyl) morpholine of formula I wherein R¹ is hydrogen with an ester of formula

R²COOR⁴ wherein R² is as above and R⁴ is $C_{1-7}$-alkyl.

R⁴ particularly is methyl.

The conversion as a rule takes place in the presence of an alkali hexamethyldisilazane such as lithium, sodium or potassium hexamethyldisilazane and a suitable organic solvent such as ethereal solvents like tetrahydrofuran, 2-methyl-tetrahydrofuran, cyclopentyl methyl ether or tert. butyl methyl ether. The reaction is usually performed at about −50° C. to −78° C.

Compounds of the formula XXX can for instance be prepared by converting the chiral 2-(4-aminophenyl) morpholine of formula

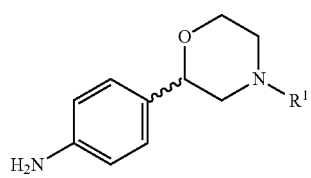

I wherein R¹ is as defined above with a halide of the formula

R²X wherein R² is as above and X is halogen.

X particularly has the meaning of chlorine.

The reaction is as a rule performed in the presence of a suitable tertiary amine such as with triethylamine, N,N-diisopropylethylamine or the like and a polar aprotic solvent such as tetrahydrofuran, ethylacetate, dimethylformamide or a polar protic solvent such as aliphatic alcohols, particularly tertiary alcohols like 2-methyl-2-butanol or the like. The reaction is as a rule performed under reflux conditions.

In a subsequent step the amino protecting group can be removed applying methods described under step e) above.

EXAMPLES

Abbreviations

CPME=cyclopentyl methyl ether
DIPEA=diisopropylethylamine
EtOH=ethanol
IPC=in process control
HPLC=high pressure liquid chromatography
TEA=triethylamine
TFA=trifluoro acetic acid
TBME=tert.butyl methyl ether
THF=tetrahydrofuran
2-Me-THF=2-methyl tetrahydrofuran
rt=room temperature Example 1

(R)-2-Bromo-1-(4-nitro-phenyl)-ethanol

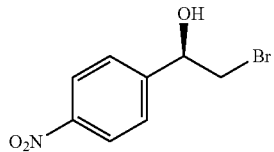 [SMILES: O=[N+]([O-])c1ccc([C@@H](O)CBr)cc1]

The substrate, 100 g 2-Bromo-1-(4-nitro-phenyl)-ethanone, was suspended in the biphasic reaction mixture of 600 ml aqueous buffer (2.45 g potassium dihydrogen phosphate (30 mM), 1.29 g magnesium acetate tetrahydrate (10 mM), 100 g D-glucose monohydrate and 100 mg NAD) and 200 ml n-heptane. Under stirring the temperature was increased to 30° C. and the pH was adjusted to 7.2 (15.7 ml 1 N NaOH). The reduction was started by the addition of the oxidoreductase KRED-Y2 [Codexis] (1.0 g) and the cofactor regeneration enzyme—glucose dehydrogenase (1.0 g GDH 105 [Codexis]) forming a fine light yellow suspension. During the 18 h reaction time the pH was kept at pH 7.2 by the addition of 403 ml 1M NaOH achieving nearly complete conversion (IPC: 0.8 area % II). After cooling to room temperature the product was filtered, washed with twice with 118 ml water and 118 ml heptane and dried under moving at a vacuum 20 mbar and 30° C. to yield in 97.7 g of the title compound. GC-EI-MS: 245 (M+H)⁺; chiral HPLC: ee 99.9% [268 nm; Chiracel OZ-H; 250*4.6 mm, isocratic 90% n-heptane, 5% EtOH, 5% n-heptane with 0.4% TFA]; 12° C.: 1 ml/min containing corresponding 2.6% (R)-epoxide IIIb, ee 99.9%.

Example 2

(S)-2-Bromo-1-(4-nitro-phenyl)-ethanol

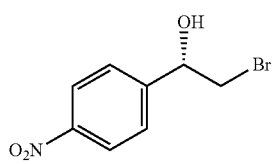

A light yellow suspension of 100 g 2-Bromo-1-(4-nitrophenyl)-ethanone in 300 ml aqueous buffer (100 mM Potassium dihydrogen phosphate pH 7.2; 2 mM Magnesium chloride) and 100 ml 2-Propanol formed under vigorous stirring. The reaction solution was heated to 30° C. and stirred for 15 min. and the actual pH was 7.7. Subsequently the reduction started by the addition of the oxidized cofactor NADP (200 mg [Roche]) and oxidoreductase (500 mg KRED-Y1 [Codexis]). The pH decreased to pH 6.5 during the course of the reaction within 23 h achieving nearly complete conversion (IPC: 1.6 area % II). After cooling to room temperature the reaction mixture was transferred—including rinsing the 4-necked flat bottomed reaction flask three times with 100 ml water—into a round bottom flask to evaporate the organic solvents, 2-Propanol and acetone (formed), at 100-50 mbar, 40° C. within 30 min. After cooling to room temperature the product was filtered, washed with 200 ml water and 200 ml heptane and dried applying high vacuum to yield in 96.6 g of the title compound. GC-EI-MS: 245 (M+H)$^+$; chiral HPLC: ee 99.5% [268 nm; Chiracel OZ-H; 250*4.6 mm, isocratic 90% n-heptane, 5% EtOH, 5% n-heptane with 0.4% TFA]; 12° C.: 1 ml/min containing corresponding 1.2% (S)-epoxide ee>99.5%.

Example 3

Example 3.1

Preparation of (S)-2-(4-nitrophenyl)oxirane

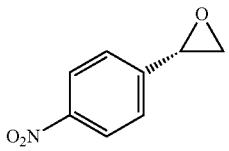

2.46 g (10.0 mmol), (S)-2-bromo-1-(4-nitrophenyl)ethanol was solved in 12.0 ml THF, at room temperature 10.0 ml 2M NaOH was added, the reaction mixture was stirred at room temperature for 1 h. The dark brown cloudy solution was filtered over a glass fiber filter, washed with 20 ml TBME, the organic layer was separated and washed with 20 ml 1M KH$_2$PO$_4$, dried over Na$_2$SO$_4$, filtered and concentrated in vacuo at 40° C./20 mbar/1 h to obtain 1.60 g of the title product as yellow solid.

MS-ESI$^-$: MH$^-$164.035

Chirality was determined with chiral HPLC with a Chiralpak IA-3 column. Enantiomeric ratio: 99.8/0.2% (S/R)

Example 3.2

Preparation of (R)-2-(4-nitrophenyl)oxirane

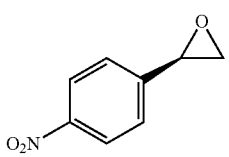 [SMILES: O=[N+]([O-])c1ccc([C@@H]2CO2)cc1]

To a solution of (R)-2-bromo-1-(4-nitrophenyl)ethanol (2.46 g, 10 mmol, Eq: 1.00) in THF (10.9 g, 12.3 ml) was added at rt NaOH (10.0 ml, 20.0 mmol, Eq: 2) and the mix stirred at rt for 1 h.

The mix was filtered and the cake washed with 20 ml TBME. The filtrate was extracted and separated, the org.-layer was washed with 20 ml of a 1M KH$_2$PO$_4$, dried over Na$_2$SO$_4$, filtered and the filtrate concentrated in vacuo at 40° C./20 mbar/1 h to obtain 1.5 g of the title product as yellow solid.

MS-ESI$^-$: MH$^-$164.035

Chirality was determined with chiral HPLC with a Chiralpak IA-3 column. Enantiomeric ratio: 99.95/0.05 (R/S)

Example 4

Example 4.1

Preparation of (S)-2-(2-hydroxyethylamino)-1-(4-nitrophenyl)ethanol

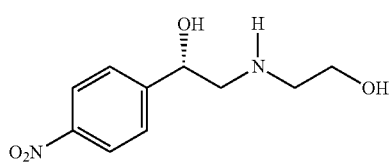

To 124.0 g (2.02 mol) 2-aminoethanol was added a solution of 50.0 g (202 mmol) (S)-2-bromo-1-(4-nitrophenyl)ethanol in 50 ml THF dropwise over a period of 30 minutes. The mixture was cooled with a water bath to keep the temperature <30° C. The mixture was stirred for 16 h at room temperature. The solution was extracted with 500 ml ethyl acetate and 500 ml water. The aqueous layer was re-extracted with 250 ml ethyl acetate. The aqueous layer was saturated with 160 g NaCl and re-extracted again with 500 ml ethyl acetate. The combined organic layers were dried over Na$_2$SO$_4$, filtered and concentrated in vacuo at 20 mbar/40° C./2 hours to obtain crude 45.05 g (S)-2-(2-hydroxyethylamino)-1-(4-nitrophenyl)ethanol as brown oil, which was used in example 5.1 without further purification.

MS-ESI$^+$: MH$^+$227.3

Example 4.2

Preparation of (R)-2-(2-hydroxyethylamino)-1-(4-nitrophenyl)ethanol

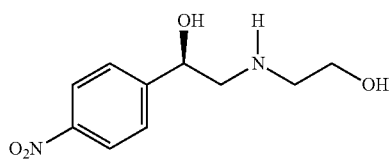 [SMILES: O=[N+]([O-])c1ccc([C@@H](O)CNCCO)cc1]

In analogy to example 4.1 (R)-2-bromo-1-(4-nitrophenyl)ethanol was reacted with 2-amino ethanol. 110 g title product was obtained as crude brown oil, which was used in example 5.2 without further purification.

MS-ESI$^+$: MH$^+$227.3

Example 5

Example 5.1

Preparation of (S)-tert-butyl 2-hydroxy-2-(4-nitrophenyl)ethyl(2-hydroxyethyl)carbamate

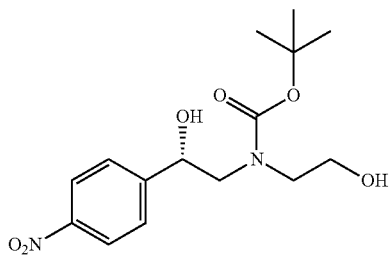 [SMILES: CC(C)(C)OC(=O)N(CCO)C[C@@H](O)c1ccc([N+](=O)[O-])cc1]

To a mixture of 45.0 g (199 mmol) (S)-2-(2-hydroxyethylamino)-1-(4-nitrophenyl)ethanol (45 g, 199 mmol, Eq: 1.00) in THF (399 g, 450 ml, 5.51 mol, Eq: 27.7) was added Boc-anhydrid (43.8 g, 46.6 ml, 201 mmol, Eq: 1.01). The temperature rose to 35° C. After 15 minutes Boc-anhyrid (6.95 g, 31.8 mmol, Eq: 0.16) was added again and the reaction was stirred for 30 minutes at room temperature. 650 ml TBME and 650 ml 1M $Na_2CO_3$ solution was added and stirred for 10 minutes. The organic layer was separated and dried over $Na_2SO_4$, filtered and concentrated in vacuo. The water was removed by azeotropic vacuo distillation with 2×100 ml TBME. The red viscous oil was dried at 40° C./12 mbar for 4 hours to obtain crude 75.26 g (S)-tert-butyl 2-hydroxy-2-(4-nitrophenyl)ethyl(2-hydroxyethyl)carbamat as brown oil, which was used in example 6.1 and 7.1 without further purification.

MS-ESI⁻: MHCOO⁻371.1

Example 5.2

Preparation of (R)-tert-butyl 2-hydroxy-2-(4-nitrophenyl)ethyl(2-hydroxyethyl)carbamate

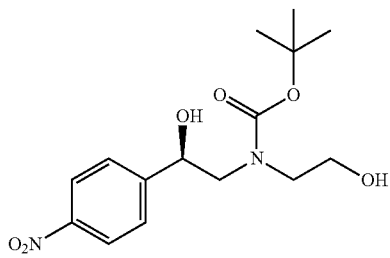 [SMILES: CC(C)(C)OC(=O)N(CCO)C[C@H](O)c1ccc([N+](=O)[O-])cc1]

In analogy to example 5.1 (R)-2-(2-hydroxyethylamino)-1-(4-nitrophenyl)ethanol was reacted with Boc-anhydride.55.6 g of the title product was obtained, which was used in example 6.2 and 7.2 without further purification.

MS-ESI⁻: (M+HCOO)⁻371.1

Example 5.3

Preparation of (S)-2-(benzyl(2-hydroxyethyl)amino)-1-(4-nitrophenyl)ethanol (from (S)-2-bromo-1-(4-nitrophenyl)ethanol)

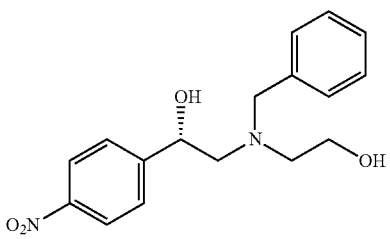

24.6 g (100 mmol) (S)-2-bromo-1-(4-nitrophenyl)ethanol was solved in 120 ml 2-propanol was added 13.9 ml (100 mmol) triethylamine and 17.1 ml (120 mmol) 2-(benzylamino)ethanol and the reaction mixture was refluxed for 16 h. The reaction mixture was cooled to room temperature; 2-propanol was removed in vacuo at 40° C./100-50 mbar/1 h. The residue was treated with 320 ml of 1.75M $NH_3$ in brine (mix of 130 ml aqueous ammonia 25% and 870 ml brine) and extracted twice with 320 ml TBME. The combined organic layer were dried over $Na_2SO_4$, filtered and the filtrate concentrated in vacuo at 40° C./20 mbar/2 h to obtain crude 30.5 g (S)-2-(benzyl(2-hydroxyethyl)amino)-1-(4-nitrophenyl)ethanol as dark red oil was used without further purification.

MS-ESI⁺: MH⁺317.15

Chirality was determined with chiral HPLC with a Chiralpak AY-3 column. Enantiomeric ratio: 91.6/8.4 (S/R).

Example 5.4

Preparation of (S)-2-(benzyl(2-hydroxyethyl)amino)-1-(4-nitrophenyl)ethanol (from (S)-2-(4-nitrophenyl)oxirane)

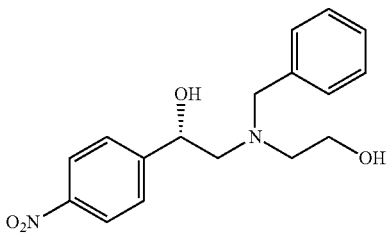 [SMILES: O=[N+]([O-])c1ccc([C@H](O)CN(CCO)Cc2ccccc2)cc1]

0.16 g g (1.0 mmol) (S)-2-(4-nitrophenyl)oxirane was solved in 0.65 ml 2-propanol, 0.14 ml (1.0 mmol) triethylamine and 0.18 ml (1.2.0 mmol) 2-(benzylamino)ethanol was added and the reaction mixture was refluxed for 16 h. The reaction mixture was cooled to room temperature; 2-propanol was removed in vacuo at 40° C./100-50 mbar/1 h. The residue was treated with 3.5 ml of 1.75M $NH_3$ in brine (mix of 130 ml aqueous ammonia 25% and 870 ml brine) and extracted twice with 3.5 ml MTBE. The combined organic layer were dried over $Na_2SO_4$, filtered and the filtrate concentrated in vacuo at 40° C./20 mbar/2 h to obtain crude 0.34 g (S)-2-(benzyl(2-hydroxyethyl)amino)-1-(4-nitrophenyl)ethanol as dark red oil was used without further purification.

MS-ESI+: MH+317.15

Chirality was determined with chiral HPLC with a Chiralpak AY-3 column. Enantiomeric ratio: 99.7/0.3 (S/R).

Example 6

Example 6.1

Preparation of (S)-tert-butyl 2-mesyloxy-2-(4-nitrophenyl)ethyl(2-hydroxyethyl)carbamate

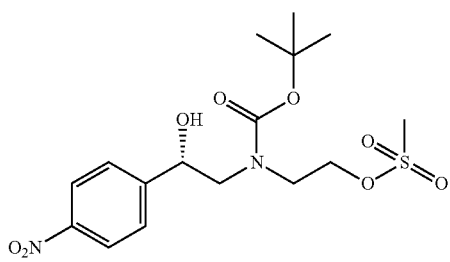 [SMILES: CC(C)(C)OC(=O)N(CCOS(C)(=O)=O)C[C@@H](O)c1ccc([N+](=O)[O-])cc1]

To a solution of 0.32 g (1.0 mmol) (S)-tert-butyl 2-hydroxy-2-(4-nitrophenyl)ethyl(2-hydroxyethyl)carbamate in 3.3 ml THF was added 0.15 ml (1.1 mmol) triethylamine, the solution was cooled to 0-5° C.

Then a solution of 82 µl, 1.05 mmol methanesulfonyl chloride in 82 µl, 1.05 mmol THF was added over a period of 5 minutes (temperature 0-5° C.). The mixture was stirred for 15 min at 0-5° C., after HPLC analysis, 23% educt left. To the white suspension 42 µl, 0.30 mmol triethylamine and 20 µl, 0.25 mmol methanesulfonyl chloride was added slowly. The suspension was stirred for 15 min at 0-5° C., filtered and washed with precooled (0-5° C.) THF. The mother liquid with crude (S)-tert-butyl 2-mesyloxy-2-(4-nitrophenyl)ethyl(2-hydroxyethyl)carbamate in solution was stored at −20° C. (the product in substance is unstable, in solution stable for several days).

MS-ESI−: (M+HCOO)−449.12

Example 6.2

Preparation of (R)-tert-butyl 2-mesyloxy-2-(4-nitrophenyl)ethyl(2-hydroxyethyl)carbamate

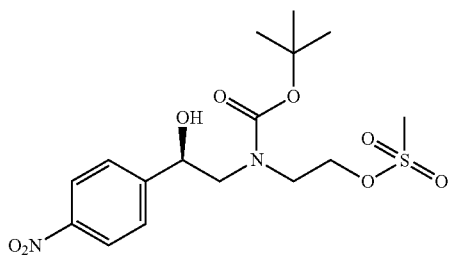 [SMILES: CC(C)(C)OC(=O)N(CCOS(C)(=O)=O)C[C@H](O)c1ccc([N+](=O)[O-])cc1]

In analogy to example 6.1 (R)-tert-butyl 2-hydroxy-2-(4-nitrophenyl)ethyl(2-hydroxyethyl)carbamate was reacted with methanesulfonylchloride. The mother liquid with crude (R)-tert-butyl 2-mesyloxy-2-(4-nitrophenyl)ethyl(2-hydroxyethyl)carbamate in solution was stored at −20° C.

MS-ESI−: (M+HCOO)−449.12

Example 7

Example 7.1

Preparation of (S)-tert-butyl 2-(4-nitrophenyl)morpholine-4-carboxylate

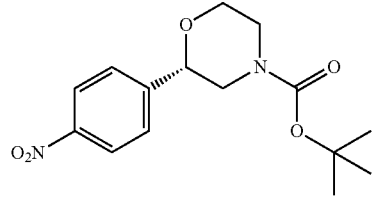 [SMILES: CC(C)(C)OC(=O)N1CCO[C@@H](c2ccc([N+](=O)[O-])cc2)C1]

To a solution of 18.0 g (55.2 mmol) (S)-tert-butyl 2-hydroxy-2-(4-nitrophenyl)ethyl(2-hydroxyethyl)carbamate in 180 ml THF, 8.50 ml (60.7 mmol) triethylamine was added and cooled to 0-5° C. A solution of 4.5 ml (57.9 mmol) methanesulfonyl chloride in 4.5.0 ml THF was added over a period of 15 minutes (temperature 0-5° C.). The mixture was stirred for 15 min. at 0-5° C. After HPLC analysis, 18% educt left. To the suspension 2.3 ml (16.5 mmol) triethylamine and 0.86 ml (11.0 mmol) methanesulfonyl chloride was added slowly. The suspension was stirred for 15 min at 0-5° C., the light yellow suspension was filtered and washed with 50 ml precooled THF (0-5° C.). To the cool solution with the intermediate (S)-tert-butyl 2-mesyloxy-2-(4-nitrophenyl)ethyl(2-hydroxyethyl)carbamate was added 27.5 ml (110 mmol) 4M NaOH and 0.38 g (1.1 mmol) tetrabutylammonium hydrogensulfate. The mixture was well stirred for 16 h at room temperature, then extracted with 140 ml water and 170 ml TBME, the separated organic layer was dried over Na$_2$SO$_4$, filtered and concentrated in vacuo at 40° C./10 mbar/2 h. The crude product 17.7 g crude product was treated with treated with 53 ml MeOH refluxed for 5 min. cooled in 1 h to room temperature and the suspension was stirred for 16 h at 0-5° C., filtered and the filter cake was washed with 13 ml precooled MeOH, the crystals were dried at 40° C./10 mbar/2 h to obtain 12.0 g of (S)-tert-butyl 2-(4-nitrophenyl)morpholine-4-carboxylate as white crystals.

GC-EI-MS: M308.+.

Chirality was determined with chiral HPLC with a Chiralpak AD-H column. Enantiomeric ratio: 99.92/0.08% (S/R).

Example 7.2

Preparation of (R)-tert-butyl 2-(4-nitrophenyl)morpholine-4-carboxylate

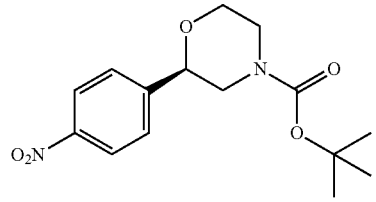 [SMILES: CC(C)(C)OC(=O)N1CCO[C@H](c2ccc([N+](=O)[O-])cc2)C1]

In analogy to example 7.1 (R)-tert-butyl 2-hydroxy-2-(4-nitrophenyl)ethyl(2-hydroxyethyl)carbamate was cyclized. 44.3 g of the title product was obtained as off white crystals.

GC-EI-MS: M308.+.

Chirality was determined with chiral HPLC with a Chiralpak AD-H column. Enantiomeric ratio: 99.95/0.05 (R/S).

Example 7.3

Preparation of (S)-4-benzyl-2-(4-nitrophenyl)morpholine hydrochloride

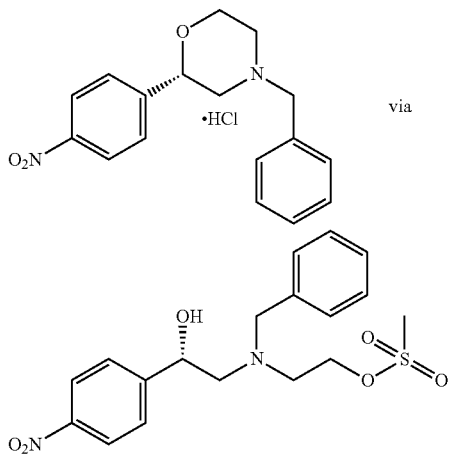

via 30.2 g (95.5 mmol) (S)-2-(benzyl(2-hydroxyethyl)amino)-1-(4-nitrophenyl)ethanol was solved in 330 ml THF, 29.3 ml (210 mmol) triethylamine was added and the solution was cooled to 0-5° C. Then a solution of 11.9 ml (153 mmol) methanesulfonyl chloride in 12 ml THF was added dropwise at 0-5° in the period of 20 min. The suspension was stirred for 30 min at 0-5° C., filtered and washed with 100 ml precooled THF. To the combined mother liquid (contain the primary mesyloxy-intermediate) was added 95 ml 4M NaOH and 0.65 g (1.91 mmol) tetrabutylammonium hydrogen sulfate. The reaction mixture was stirred for 2 h at room temperature, extracted with 300 ml water and 300 ml tert.-butyl methyl ether (TBME), the separated organic layer was dried with Na₂SO₄, filtered and the filtrate was concentrated in vacuo at 40° C./10 mbar/5 h to obtain crude 35.9 g (S)-4-benzyl-2-(4-nitrophenyl)morpholine as dark brown oil. The crude product was solved in 50 ml ethyl acetate, 24.0 ml 4M HCl in ethanol (prepared in situ with acetyl chloride in ethanol) was added. The formed suspension was refluxed for 5 min, 50 ml ethylacetate was added and refluxed again for 5 min. The suspension was cooled in 1 h to room temperature and stirred for 1 h at room temperature, filtered and washed with 25 ml solvent mix of ethyl acetate and ethanol 4/1. The crystals were dried in vacuo at 40° C./10 mbar/2 h to obtain 11.8 g (S)-4-benzyl-2-(4-nitrophenyl)morpholine hydrochloride as off-white crystals.

MS-ESI⁺: MH⁺299.1393.

Chirality was determined with chiral HPLC with a column Chiralpak AD-3. Enantiomeric ratio: 93.40/6.60% (S/R).

Example 8

Example 8.1

Preparation of (S)-tert-butyl 2-(4-aminophenyl)morpholine-4-carboxylate

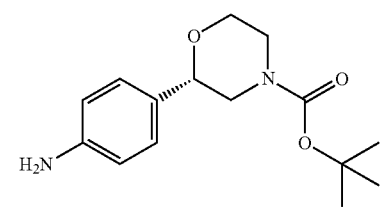

To a suspension of 6.0 g (19.5 mmol) (S)-tert-butyl 2-(4-nitrophenyl)morpholine-4-carboxylate (6.0 g, 44.1 mmol, Eq: 1.00) in 60 ml MeOH, 0.23 g Pd/C (10%) was added under argon and the mixture was stirred with hydrogen gas (1.1 bar) at 0-5° C. for 2 h, then for 16 h at room temperature. The suspension was filtered and the filtrate concentrated in vacuo at 40° C./10 mbar/2 h to obtain 5.4 g (S)-tert-butyl 2-(4-aminophenyl)morpholine-4-carboxylate as colorless resin (which crystallize after standing).

GC-EI-MS: M278.+.

Chirality was determined with chiral HPLC with a column Chiralpak IA-3. Enantiomeric ratio: 99.65/0.35% (S/R).

Example 8.2

Preparation of (R)-tert-butyl 2-(4-aminophenyl)morpholine-4-carboxylate

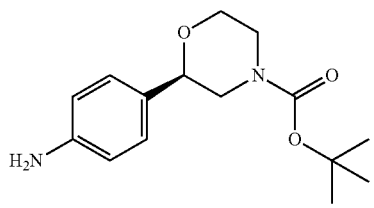

In analogy to example 8.1 (R)-tert-butyl 2-(4-nitrophenyl)morpholine-4-carboxylate was reduced to form 47.8 g of title product as light yellow oil (which crystallizes after standing).

GC-EI-MS: M278.+

Chirality was determined with chiral HPLC with a column Chiralpak IA-3. Enantiomeric ratio: 99.99/0.01 (R/S).

Example 9

Example 9.1

Preparation of (S)-2-(4-aminophenyl)morpholine (from (S)-tert-butyl-2-(4-aminophenyl)morpholine-4-carboxylate)

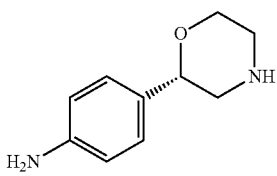 [SMILES: Nc1ccc([C@H]2CNCCO2)cc1]

16.7 g (60.0 mmol) (S)-tert-butyl-2-(4-aminophenyl)morpholine-4-carboxylate was solved in 85 ml methanol, 47 ml (360 mmol) hydrochloric acid 25% was added and the reaction mixture was refluxed for 1.5 h, cooled to 0-5° C., in 5 min 42 ml (386 mmol) 9.2M NaOH was added drop wise. To remove methanol, the suspension was concentrated in vacuo 40° C./150-50 mbar, the aqueous suspension was extracted three times with 100 ml ethyl acetate and three times with 100 ml THF, the combined organic layers were dried with $Na_2SO_4$, filtered and concentrated in vacuo at 40° C./150-10 mbar to obtain 10.65 g crude product as red solid, which was crystallize with 100 ml TBME, heated to reflux for, distilled of 70 ml TBME, the yellow suspension was stirred 1 h at room temperature, filtered and washed with 10 ml TBME, the light pink crystals were dried at 40° C./10 mbar/2 h to obtain 9.24 g (S)-2-(4-aminophenyl)morpholine.

GC-EI-MS: $M178^{·+}$.

Example 9.2

Preparation of (S)-2-(4-aminophenyl)morpholine (from(S)-4-benzyl-2-(4-nitrophenyl)morpholine hydrochloride)

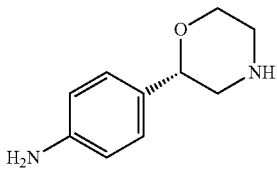 [SMILES: Nc1ccc([C@H]2CNCCO2)cc1]

11.8 g (35.2 mmol) (S)-4-benzyl-2-(4-nitrophenyl)morpholine hydrochloride was suspended in 118 ml methanol 1.18 g Pd/C 10% was added, flushed with argon and then with hydrogen gas (1.1 bar), hydrogenated at room temperature for 20 h. 12 ml water was added and hydrogenated again for 4 h. The black suspension was heated to 60° C. for 10 min, filtered over of a glass fiber filter, washed with 100 ml methanol. The filtrate was concentrated in vacuo at 40° C./10 mbar/5 h to obtain 7.50 g crude (S)-2-(4-aminophenyl) morpholine hydrochloride as yellow solid. 5.37 g (25 mmol) of the crude product was extracted with 35 ml 1M NaOH/brine solution (prepared with 500 ml brine and 500 ml 2M NaOH) and 50 ml of a mixture of THF/TBME 1/1. The aqueous layer was re-extracted 5 times with 50 ml THF/TBME 1/1. The combined organic layers were dried with $Na_2SO_4$, filtered and the filtrate was concentrated in vacuo at 40° C./10 mbar/5 h to obtain 4.25 g (S)-2-(4-aminophenyl)morpholine as light yellow crystals.

GC-EI-MS: $M178^{·+}$.

Example 10

Preparation of (S)-tert-butyl 2-(4-(2-(trifluoromethyl)isonicotinamido) phenyl)morpholine-4-carboxylate

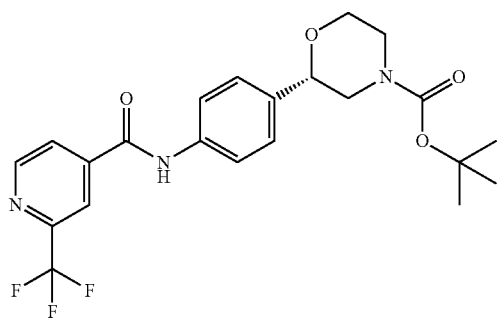 [SMILES: CC(C)(C)OC(=O)N1CCO[C@@H](c2ccc(NC(=O)c3ccnc(C(F)(F)F)c3)cc2)C1]

2.78 g (10.0 mmol) (S)-tert-butyl 2-(4-aminophenyl) morpholine-4-carboxylate was solved in 27 ml ethyl acetate, 1.91 g (10.0 mmol) 2-(trifluoromethyl)isonicotinic acid and 2.80 ml (20.0 mmol) trietyhlamine was added. At room temperature a solution of 7.70 ml (13.0 mmol) n-propylphosphonic acid anhydride (cyclic trimer) 50% in ethyl acetate (P3P®) was added, the reaction mixture was stirred for 15 h at room temperature, extracted with 45 ml water and 45 ml 1M $NaHCO_3$ solution. The organic layer was dried over $Na_2SO_4$, filtered and concentrated in vacuo at 40° C. to obtain 4.57 g as light yellow foam.

MS-ESI$^-$: (M–H)$^-$450.16

Example 11

Preparation of (S)-2-(4-(2-(trifluoromethyl)isonicotinamido)phenyl)morpholine hydrochloride

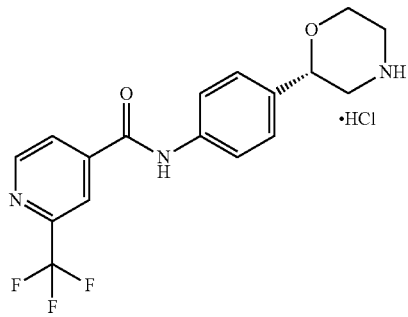 [SMILES: O=C(Nc1ccc([C@H]2CNCCO2)cc1)c1ccnc(C(F)(F)F)c1 ; Cl]

4.01 g (8.88 mmol) (S)-tert-butyl 2-(4-(2-(trifluoromethyl)isonicotinamido) phenyl) morpholine-4-carboxylate (4.01 g, 8.88 mmol, Eq: 1.00) was treated with 16.6 ml 1-propanol, 3.50 ml 26.6 mmol hydrochloric acid 25% was added the solution was stirred at 60° C. for 30 min. The solution was concentrated in vacuo 40° C./50 mbar to distill off 10 ml solvent mixture, then 10 ml 1-propanol was added and again distilled off 10 ml solvent mixture, this procedure was repeated three times. The formed suspension was heated to 60° C. for 10 min, stirred for 1 h at room temperature, filtered and washed with 5 ml 1-propanol, the white crystals were dried at 40° C./10 mbar/2 h to obtain 3.11 g (S)-2-(4-(2-trifluoromethyl)isonicotinamido)phenyl) morpholine hydrochloride.

MS-ESI⁺: (MH)⁺352.12

The chirality was determined with chiral HPLC with a column Chiralpak AY-3. Enantiomeric ratio: 99.50/0.50 (S/R).

Example 12

Example 12.1

Preparation of (R)-tert-butyl 2-(4-(6-chloro-2-(trifluoromethyl)pyrimidine-4-ylamino)phenyl)morpholine-4-carboxylate

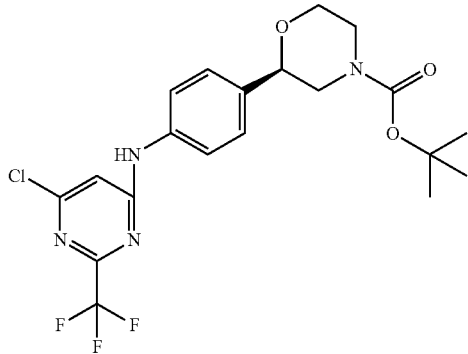 [SMILES: CC(C)(C)OC(=O)N1CCO[C@H](c2ccc(Nc3cc(Cl)nc(C(F)(F)F)n3)cc2)C1]

To a solution of 2.78 g (10 mmol) (R)-tert-butyl 2-(4-aminophenyl)morpholine-4-carboxylate in 8.4 ml 2-Methyl-2-butanol was added 2.62 ml (15.0 mmol) DIPEA and 1.58 ml (11.0 mmol) 4,6-dichloro-2-(trifluoromethyl)pyrimidine and the mix was refluxed for 1 h. The mix was diluted with 45 ml TBME and washed twice with 45 ml water. The organic layer was dried over Na₂SO₄, filtered and the filtrate concentrated in vacuo at 40° C./20 mbar/1 h. 5.13 g of the title product was obtained as yellow foam which was used in example 12.2, without further purification

MS-ESI⁺: (MH)⁺459.14

Example 12.2

Preparation of (R)-tert-butyl 2-(4-(2-(trifluoromethyl) pyrimidin-4-ylamino)phenyl)morpholine-4-carboxylate

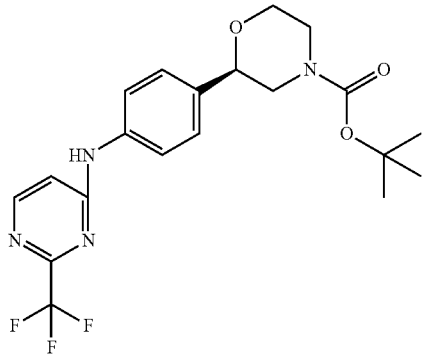 [SMILES: CC(C)(C)OC(=O)N1CCO[C@H](c2ccc(Nc3ccnc(C(F)(F)F)n3)cc2)C1]

To a solution of 3.7 g (8.06 mmol) (R)-tert-butyl 2-(4-(6-chloro-2-(trifluoromethyl)pyrimidin-4-ylamino)phenyl)morpholine-4-carboxylate 37.0 ml in 2-propanol and 1.35 ml (9.68 mmol) TEA was added 0.19 g Pd/C 10% and the mix set under a H₂ atmosphere under stirring for 1 h.

The suspension was filtered, the cake washed with 2-propanol and the filtrate concentrated in vacuo at 40° C./20 mbar/2 h. The crude was dissolved in 35 ml ethyl acetate and washed with 35 ml of a 0.25M HCl solution. The organic layer was dried over Na₂SO₄, filtered and the filtrate concentrated in vacuo at 40° C./20 mbar/1 h. The crude was stirred in 4.5 ml MeOH at rt and slowly 1.5 ml water were added dropwise. A light suspension was formed which was stirred for 16 h. The suspension was filtered and the cake washed with 1.5 ml MeOH/water and dried in vacuo at 40° C./20 mbar/3 h. 2.82 g of the title product was obtained in the form of white crystals which was used in example 12.3 without further purification.

MS-ESI⁺: (MH)⁺425.18

Example 12.3

Preparation of (R)-tert-butyl 2-(4-(2-(trifluoromethyl)pyrimidin-4-ylamino)phenyl)morpholine-4-carboxylate

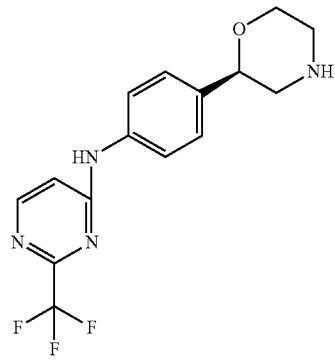 [SMILES: FC(F)(F)c1nccc(Nc2ccc([C@@H]3CNCCO3)cc2)n1]

To a solution of 2.80 g (6.60 mmol)(R)-tert-butyl 2-(4-(2-(trifluoromethyl) pyrimidin-4-ylamino)phenyl)morpholine-4-carboxylate in 28.0 ml MeOH was added 5.15 ml (39.6 mmol) HCl 25% and the mix was stirred at 60° C. for 1.5 h. The mix was concentrated in vacuo at 40° C./200-20 mbar/30 min.

To the solid slowly 40 ml Na₂CO₃ (1M) and 5 ml water were added (gas emission) and the mix extracted with 25 ml ethyl acetate treated with 5 ml EtOH. The aqueous layer was re-extracted with 10 ml ethyl acetate. The combined organic layer was dried over Na₂SO₄, filtered and the filtrate concentrated in vacuo.

The crude was stirred in 4 ml TBME treated with 200 ul EtOH at 56° C. for 20 min until a homogeneous suspension was formed. Then the mix was cooled to rt and stirred for 2 h before it was filtered, the cake washed with 1 ml TBME and dried in vacuo at 40° C./20 mbar/1 h. 1.9 g of the title product in the form of white crystals was obtained.

MS-ESI⁺: (MH)⁺325.13

The chirality was determined with chiral HPLC with a column Chiralpak IC-3. Enantiomeric ratio: 99.89/0.11 (R/S).

Example 13

Preparation of (S)-tert-butyl 2-(4-(2-(trifluoromethyl)isonicotinamido) phenyl)morpholine-4-carboxylate

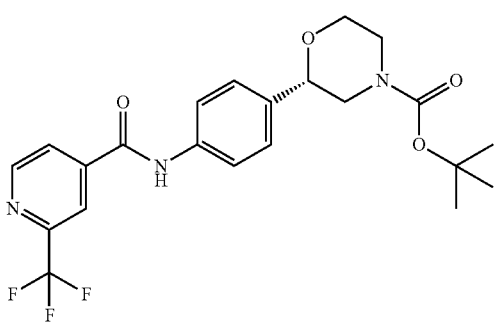

27.8 g (10.0 mmol) (S)-tert-butyl 2-(4-aminophenyl) morpholine-4-carboxylate and 22.6 g (110 mmol) methyl 2-(trifluoromethyl)isonicotinate was solved in 110 ml THF. The yellow solution was cooled to 0-5° C. A solution of 22.9 g (200 mmol) potassium tert-butoxide in 160 ml THF was added dropwise in the course of 30 min. The dark yellow solution was stirred at 0-5° C. for 1 h. In 20 min at 0-5° C., 140 ml water was added and stirred for 30 min at 0-5° C. The reaction mixture was neutralized at 0-5° C., in the course of 30 min with 97 ml (194 mmol) aq. 2M HCl, to obtain pH 7-8. The reaction mixture was extracted with 200 ml MTBE. The organic layer was separated, dried with $Na_2SO_4$, filtered and concentrated in vacuo to obtain 49.8 g crude (S)-tert-butyl 2-(4-(2-(trifluoromethyl)isonicotinamido)phenyl)morpholine-4-carboxylate as yellow foam contain some organic solvent) which was used in example 14, without further purification.

MS-ESI⁻: (M–H)⁻450.16

Example 14

Preparation of (S)-2-(4-(2-(trifluoromethyl)isonicotinamido)phenyl)morpholine hydrochloride

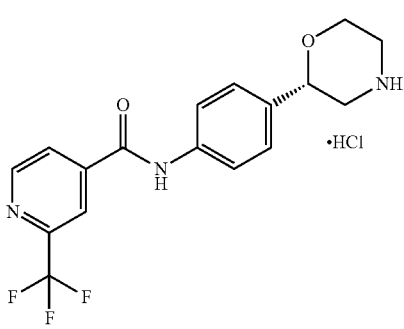 [SMILES: O=C(Nc1ccc([C@H]2CNCCO2)cc1)c1ccnc(C(F)(F)F)c1 ; Cl]

Crude 49.8 g (100.0 mmol) (S)-tert-butyl 2-(4-(2-(trifluoromethyl)isonicotinamido) phenyl) morpholine-4-carboxylate as yellow foam (from example 13) was evaporated twice with 100 ml 1-propanol to obtain a solution of 57.2 g which was solved with 170 ml 1-propanol, 39.0 ml (300 mmol) hydrochloric acid 25% was added. The mixture was heated to 55-60° C. for 2.5 hours. The suspension was transferred with 50 ml 1-propanol to a 500 ml round bottom flask and the suspension was concentrated in vacuo at 40° C./60-30 mmbar. Total 140 ml solvent mixture was removed. 150 ml 1-propanol was added and removed again in vacuo. The procedure was repeated three times. The suspension was diluted with 150 ml 1-propanol and heated to 60-65° C. for 10 min., cooled in 1 hour to r.t. and stirred for 18 hours at room temperature, the yellow suspension was filtered and the filter cake was washed portionwise with total 50 ml 1-propanol. The white crystals were dried at 40° C./15 mbar for 3 hours to obtain 35.1 g (S)-2-(4-(2-trifluoromethyl) isonicotinamido)phenyl) morpholine hydrochloride.

MS-ESI⁺: (MH)⁺352.12.

The chirality was determined with chiral HPLC with a column Chiralpak AY-3. Enantiomeric ratio: 99.60/0.40 (S/R).

Example 15

Preparation of (S)-2-(4-(2-(chloro)isonicotinamido) phenyl)morpholine

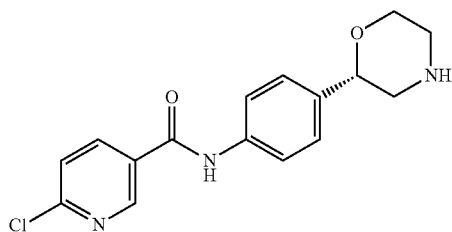 [SMILES: O=C(Nc1ccc([C@H]2CNCCO2)cc1)c1ccc(Cl)nc1]

178 mg (1.0 mmol) (S)-2-(4-aminophenyl)morpholine was solved in 4.0 ml THF and 172 mg (1.0 mmol) methyl 6-chloronicotinate was added. The yellow solution was cooled to −70 to −78° C. To the yellow suspension 2.0 ml 1M lithium hexamethyldisilazan solution in THF was added in the course of 30 min, stirred for 1 h at −70 to −78° C. 2.0 ml 1M HCl was added and the organic layer was separated, the water layer was extracted again with 2.0 ml ethyl acetate, the combined organic layer were dried with $Na_2SO_4$, filtered and concentrated in vacuo at 40° C. to obtain crude 290 mg product as light yellow solid. The crude product was treated with 3.0 ml toluene heated to reflux, then cooled to r.t. stirred for 2 h at r.t., filtered and washed with 1.0 ml toluene, dried at 40° C./2 h to obtain 270 mg as white crystals.

MS-ESI⁺: (MH)⁺318.10.

The chirality was determined with chiral HPLC with a column Chiralpak AY-3. Enantiomeric ratio: 94.77/5.23 (S/R).

We claim:

1. A process for the preparation of a chiral 2-(4-aminophenyl) morpholine of formula (I)

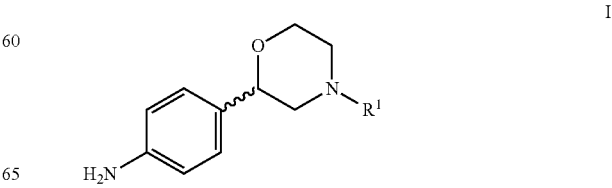

wherein R$^1$ is hydrogen or an amino protecting group (PG) said process comprising the steps of:

(a) reducing a ketone of the formula II wherein X is a halogen atom with an

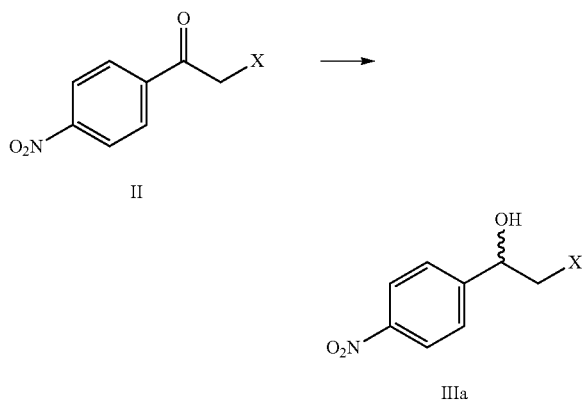

II

IIIa ketoreductase enzyme to afford the chiral alcohol of the formula IIIa;

(b) displacing the halogen intramolecularly followed by in situ ring opening

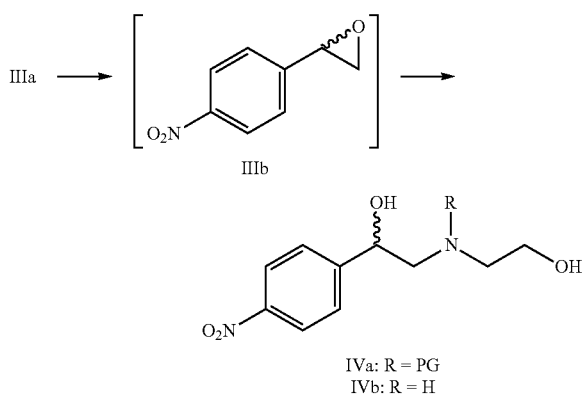

IIIb

IVa: R = PG
IVb: R = H of the resulting epoxide IIIb with ethanolamine to afford IVb;

(c) introducing a protecting group to afford IVa wherein PG is an amino protecting group;

(d) contacting IVa with R$^3$SO$_2$X wherein X is a halogen to afford VI;

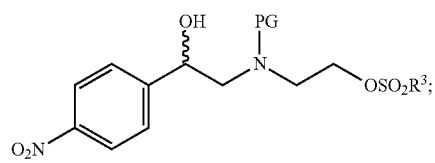

VI: R$^3$ = C$_{1-4}$ alkyl or optionally substituted phenyl (e) cyclizing VI to afford the chiral morpholine V wherein PG is as defined

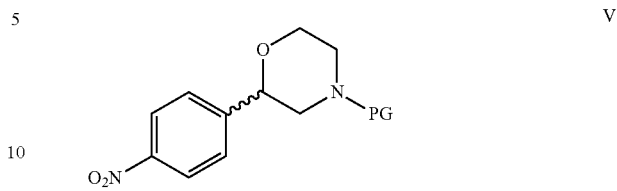

V above;

(f) reducing the nitro group to afford chiral 2-(4-aminophenyl) morpholine of the formula I wherein R$^1$ is an amino PG; and, (g) optionally removing the amino protecting group PG to afford a compound of formula I wherein R$^1$ is a H.

2. The process of claim 1, wherein the amino protecting group is selected from Boc (t-butoxycarbonyl), benzyl, 4-methoxybenzyl, benzhydryl, Fmoc (fluorenylmethoxycarbonyl), Cbz (benzyloxycarbonyl), Moz (p-methoxybenzyl carbonyl), Troc (2,2,2-trichloroethoxycarbonyl), Teoc (2-(trimethylsilyl)ethoxycarbonyl), Adoc (adamantoxycarbonyl), formyl, acetyl or cyclobutoxycarbonyl.

3. The process of claim 2, wherein the amino protecting group is Boc or benzyl.

4. The process of claim 1, wherein said ketoreductase converts the ketone of formula II into the chiral alcohol of formula IIIa with an enantiomeric excess of at least 98%.

5. The process of claim 1, wherein the enzymatic reduction in step a) is performed in the presence of NADH or NADPH as co-factor.

6. The process of claim 5, wherein the co-factor is regenerated with a cosubstrate selected from a secondary alcohol or from an additional enzyme selected from alcohol dehydrogenase, glucose dehydrogenase, formate dehydrogenase, glucose-6-phosphate dehydrogenase, phosphite dehydrogenase or hydrogenase.

7. The process of claim 6, wherein the enzymatic reduction is performed in an aqueous medium in the presence of an organic co-solvent at temperatures of 1° C. to 50° C.

8. The process of claim 7, wherein a homogeneous suspension is formed.

9. The process of claim 1, wherein the chiral carbon is either the (R) or (S) configuration with an enantiomeric excess of at least 98%.

10. The process of claim 1 wherein the intermediate epoxide in step (b) is isolated, converted to ethanolamine IVb which is isolated and the protecting group is introduced in a third step to afford IVa.

11. The process of claim 10, wherein:
(i) the epoxide is formed using an alkali hydroxide as base;
(ii) the ethanolamine IVb is formed in an organic solvent at a temperature of 0° C. to 60° C. using an excess of 2 to 30 equivalents of ethanolamine,
(iii) the protecting group is Boc and which is introduced in the presence of an organic solvent at a temperature of 0° C. to 40° C.

12. The process of claim 1 wherein the alcohol IIIa is converted to ethanolamine IVb in situ without isolation of the epoxide and IVb is isolated and the protecting group is introduced in a second step to afford IVa.

13. The process of claim 12 wherein:
(i) the first step is performed in the presence of an organic solvent at a temperature of 0° C. to 60° C. using an excess of 2 to 30 equivalents of ethanolamine, (ii) the second step is introduction of the Boc amino protecting group PG in the presence of an organic solvent at a temperature of 0° C. to 40° C.

14. The process of claim 1 wherein the alcohol IIIa is converted to the N-protected ethanolamine IVa in situ without isolation of the epoxide by contacting IIIb with an N-protected ethanolamine of the formula

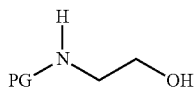

wherein PG stands for an amino protecting group.

15. The process of claim 14, wherein to the N-protected ethanolamine IVa is N-benzylethanolamine and is introduced in the presence of an organic base, an organic solvent, at a temperature of between 40° C. and the reflux temperature of the solvent.

16. The process of claim 1, wherein (i) step (d) is carried out by reacting the N-protected ethanolamine compound of formula IVb with a sulfonyl chloride of the formula $R^3$—$SO_2Cl$ in the presence of an organic base and an organic solvent at a temperature of 0° C. to 40° C. to form an sulfonate of the formula VI

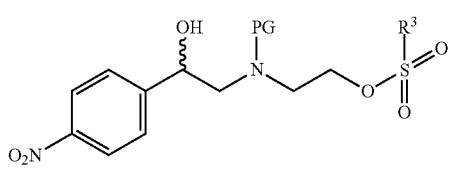

wherein PG is as defined above and $R^3$ is $C_{1-4}$ alkyl or phenyl optionally substituted with a $C_{1-4}$ alkyl group, with a nitro group or with a halogen atom; and (ii) the subsequent cyclization of VI is accomplished with a non-nucleophilic base at a temperature of 0° C. to 40° C.

17. The process of claim 1, wherein the reduction of the nitro group in step (f) is performed with hydrogen in the presence of a metal hydrogenation catalyst and an organic solvent.

18. A process for the preparation of a compound of formula XX

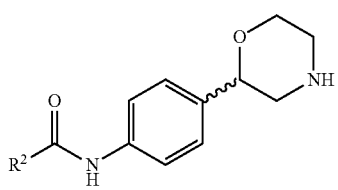

wherein:
R² is aryl or heteroaryl, wherein the aromatic rings are optionally substituted by one or two substituents, selected from $C_{1-7}$-alkyl, halogen, $CF_3$, $OCF_3$, $OCH_2CF_3$, $C_{1-7}$-alkoxy or cyano; or a pharmaceutically suitable acid addition salt thereof, comprising the steps of:

(a) reducing a ketone of the formula (II) wherein X is a halogen atom with an

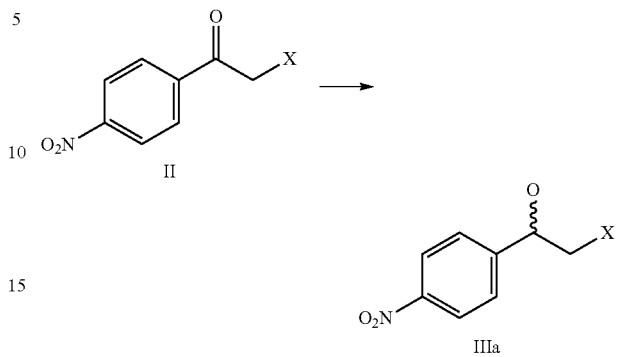

ketoreductase enzyme to afford the chiral alcohol of the formula (IIIa);

(b) displacing the halogen intramolecularly followed by in situ ring opening of the resulting epoxide IIIb with ethanolamine to afford IVb

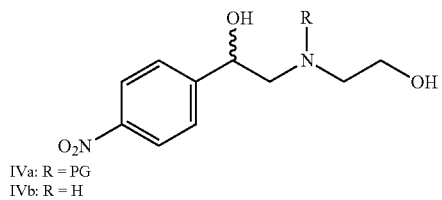

IVa: R = PG
IVb: R = H (c) introducing a protecting group to afford IVa wherein PG is an amino protecting group;
(d) contacting IVa with $R^3SO_2X$ wherein X is a halogen to afford VI

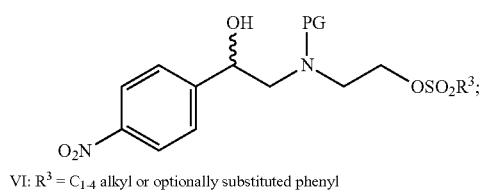

VI: $R^3$ = $C_{1-4}$ alkyl or optionally substituted phenyl (e) cyclizing VI to afford the morpholine V wherein PG is as defined above

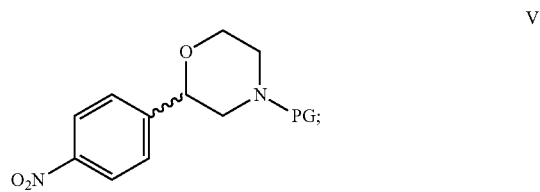

(f) reducing the nitro group to form the chiral 2-(4-aminophenyl) morpholine of the formula I wherein $R^1$ is a PG;
(g) removing the amino protecting group PG to afford a compound of formula I wherein $R^1$ is a H; and, (h) treating I with an ester of formula R² COOR⁴ wherein R² is as above and R⁴ is $C_{1-7}$-alkyl or with a carboxylic acid of the formula R² COOH to afford a compound of formula XX.

19. A process for the preparation of a compound of formula XXX comprising

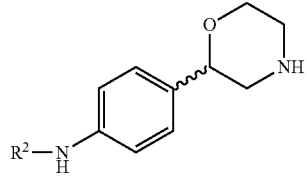

XXX wherein:

R² is aryl or heteroaryl, wherein the aromatic rings are optionally substituted by one or two substituents, selected from $C_{1-7}$-alkyl, halogen, $CF_3$, $OCF_3$, $OCH_2CF_3$, $C_{1-7}$-alkoxy or cyano; or a pharmaceutically suitable acid addition salt thereof, comprising the steps of:

(a) reducing a ketone of formula II wherein X is a halogen atom with an

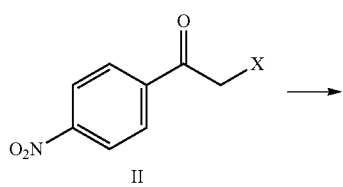

II

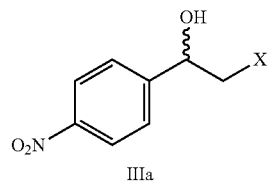

IIIa ketoreductase enzyme to afford the chiral alcohol of the formula IIIa;

(b) displacing the halogen intramolecularly followed by in situ ring opening of the

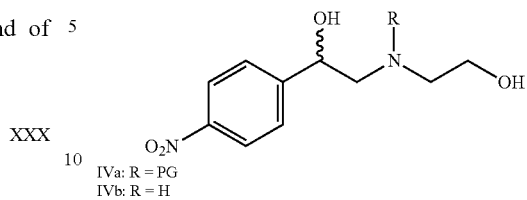

IVa: R = PG
IVb: R = H resulting epoxide IIIb with ethanolamine to afford IVb;

(c) introducing a protecting group to afford IVa wherein PG is an amino protecting group;

(d) contacting IVa with $R^3SO_2X$ wherein X is a halogen to afford VI

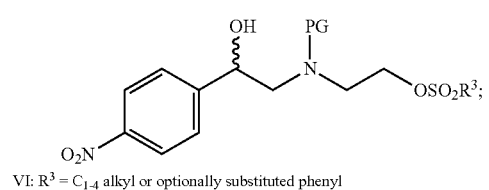

VI: $R^3$ = $C_{1-4}$ alkyl or optionally substituted phenyl (e) cyclizing VI to afford the morpholine V wherein PG is as defined above

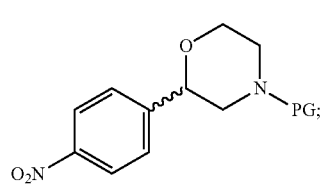

V (f) reducing the nitro group to form the chiral 2-(4-aminophenyl) morpholine of the formula I wherein R¹ is a PG;

(g) removing of the amino protecting group PG to afford a compound of formula I wherein R¹ is a H; and, (h) treating I with R² X wherein R² is as above and X is halogen to afford a compound of formula XXX.

* * * * *